United States Patent
Nguyen

(10) Patent No.: US 6,522,933 B2
(45) Date of Patent: Feb. 18, 2003

(54) STEERABLE CATHETER WITH A CONTROL HANDLE HAVING A PULLEY MECHANISM

(75) Inventor: Frank Nguyen, Chino Hills, CA (US)

(73) Assignee: Biosense, Webster, Inc., Diamond Bar, CA (US)

( * ) Notice: Subject to any disclaimer, the term of this patent is extended or adjusted under 35 U.S.C. 154(b) by 5 days.

(21) Appl. No.: 09/822,087

(22) Filed: Mar. 30, 2001

(65) Prior Publication Data

US 2002/0143378 A1 Oct. 3, 2002

(51) Int. Cl.[7] .............................. A61N 1/00; A61B 1/00
(52) U.S. Cl. .................. 607/116; 600/146; 600/149
(58) Field of Search ................ 607/116; 604/170.3; 600/101, 129, 139, 146, 149

(56) References Cited

U.S. PATENT DOCUMENTS

| | | | |
|---|---|---|---|
| 4,499,895 A | 2/1985 | Takayama ..................... 128/6 |
| 4,941,455 A | 7/1990 | Watanabe et al. ............. 128/4 |
| 4,942,866 A | 7/1990 | Usami ........................... 128/4 |
| 4,996,974 A | 3/1991 | Ciarlei .......................... 128/4 |
| 5,167,221 A | 12/1992 | Chikama ....................... 128/4 |
| 5,255,668 A | 10/1993 | Umeda .......................... 128/4 |
| 5,462,527 A | 10/1995 | Stevens-Wright et al. ..... 604/95 |
| 5,507,725 A | 4/1996 | Savage et al. ................. 604/95 |
| 5,520,222 A | 5/1996 | Chikama ..................... 138/118 |
| 5,562,619 A | 10/1996 | Mirarchi et al. ............... 604/95 |
| 5,571,085 A | 11/1996 | Accisano, III ................ 604/95 |
| 5,662,116 A | 9/1997 | Kondo et al. ........... 128/662.06 |
| 5,666,970 A | 9/1997 | Smith .......................... 128/772 |
| 5,667,476 A | 9/1997 | Frassica et al. .............. 600/149 |
| 5,741,320 A | 4/1998 | Thornton et al. ............ 607/122 |
| 5,752,912 A | 5/1998 | Takahashi et al. ........... 600/149 |
| 5,865,800 A | 2/1999 | Mirarchi et al. ............... 604/95 |
| 5,868,760 A | 2/1999 | McGuckin, Jr. ............. 606/139 |
| 5,904,667 A | 5/1999 | Falwell ......................... 604/95 |
| 5,906,590 A | 5/1999 | Hunjan et al. ................. 604/95 |
| 5,944,690 A | 8/1999 | Falwell et al. ................. 604/95 |
| 6,013,052 A | 1/2000 | Durman et al. ................ 604/95 |
| 6,083,170 A | 7/2000 | Ben-Haim ................... 600/463 |

Primary Examiner—Teresa Walberg
Assistant Examiner—Thor Campbell
(74) Attorney, Agent, or Firm—Christie, Parker & Hale, LLP

(57) ABSTRACT

A steerable catheter is provided. The catheter comprises an elongated, flexible tubular catheter body having proximal and distal ends and a lumen extending therethrough and a control handle at the proximal end of the catheter body. The control handle comprises a handle housing having a generally hollow interior and fixedly attached, either directly or indirectly to the catheter body; a piston slidably mounted in the handle housing and having proximal and distal ends; and a pulley fixedly attached, either directly or indirectly to the handle housing at a location proximal to the proximal end of the piston. A first puller wire is provided having a distal end fixedly attached in the distal end of the catheter body and a proximal end anchored to the piston. A second puller wire is provided having a distal end fixedly attached in the distal end of the catheter body. The second puller wire extends through the catheter body, into the handle, and around the pulley, and the proximal end of the second puller wire is anchored to the piston.

35 Claims, 14 Drawing Sheets

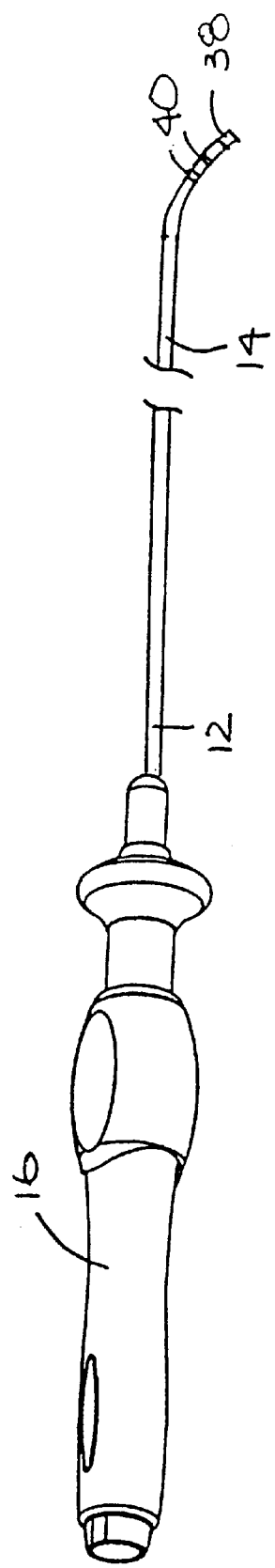

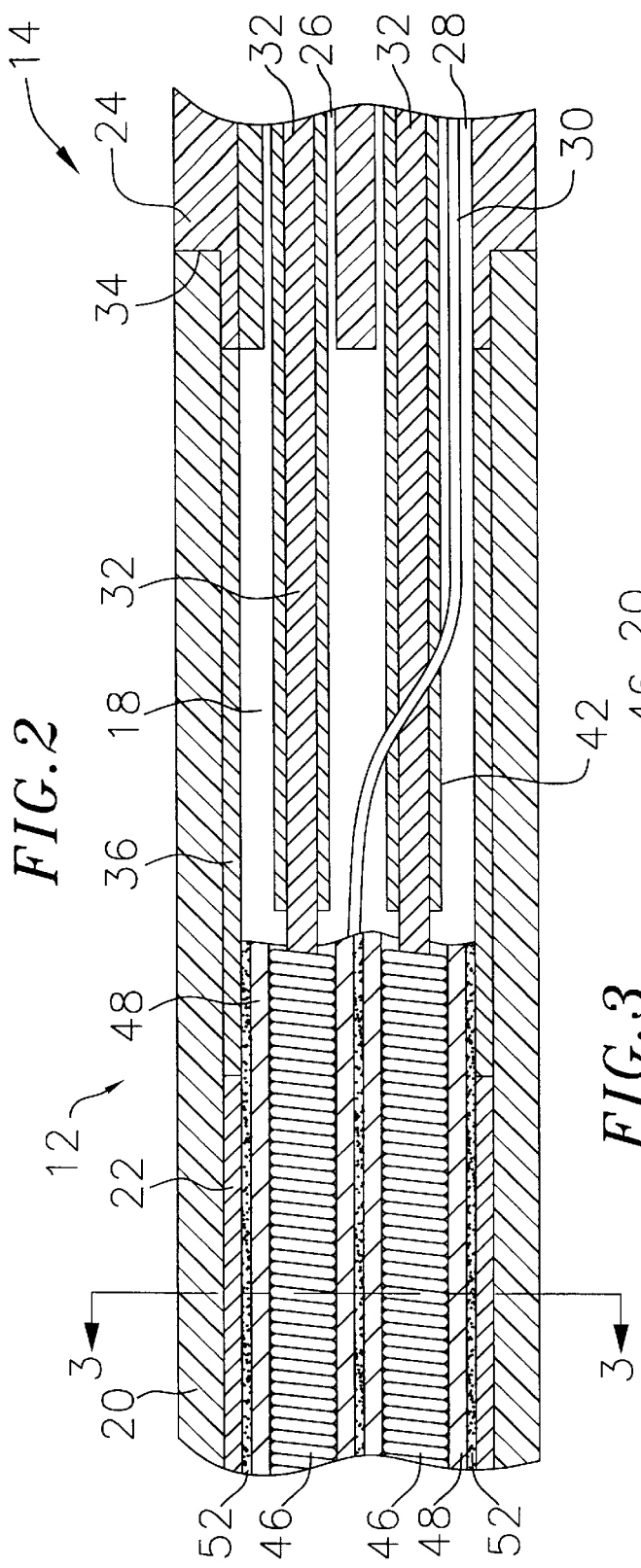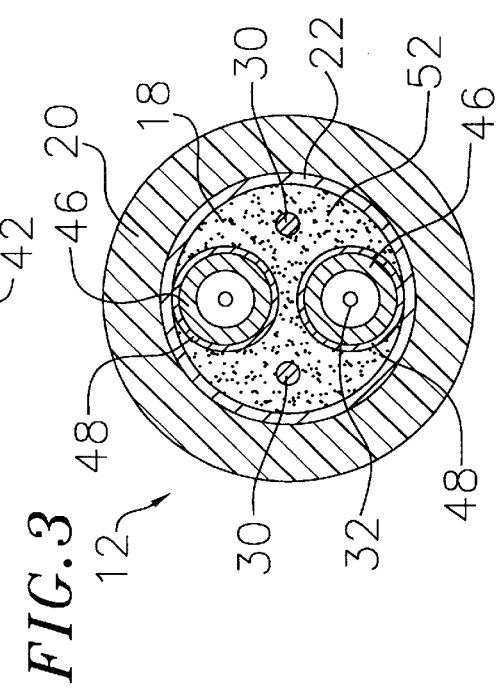

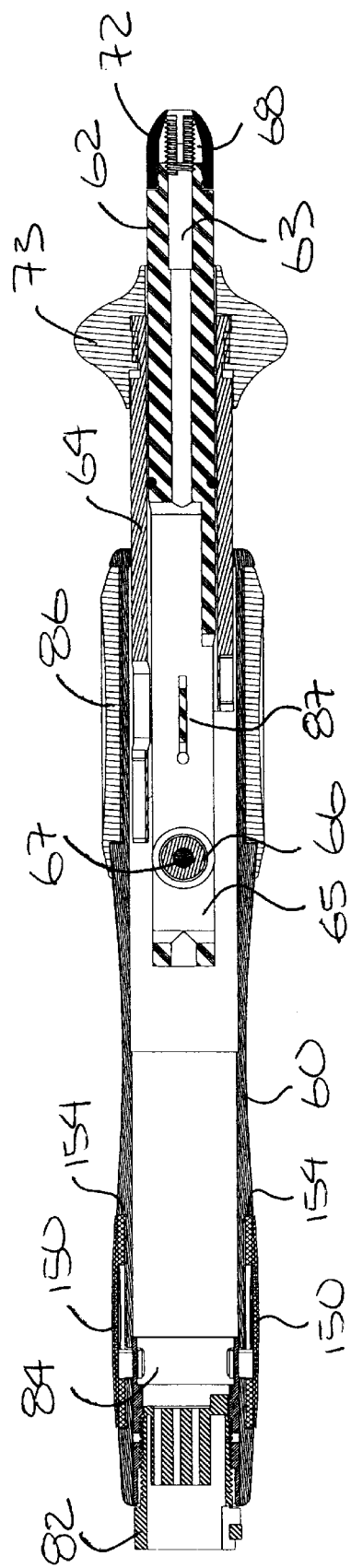

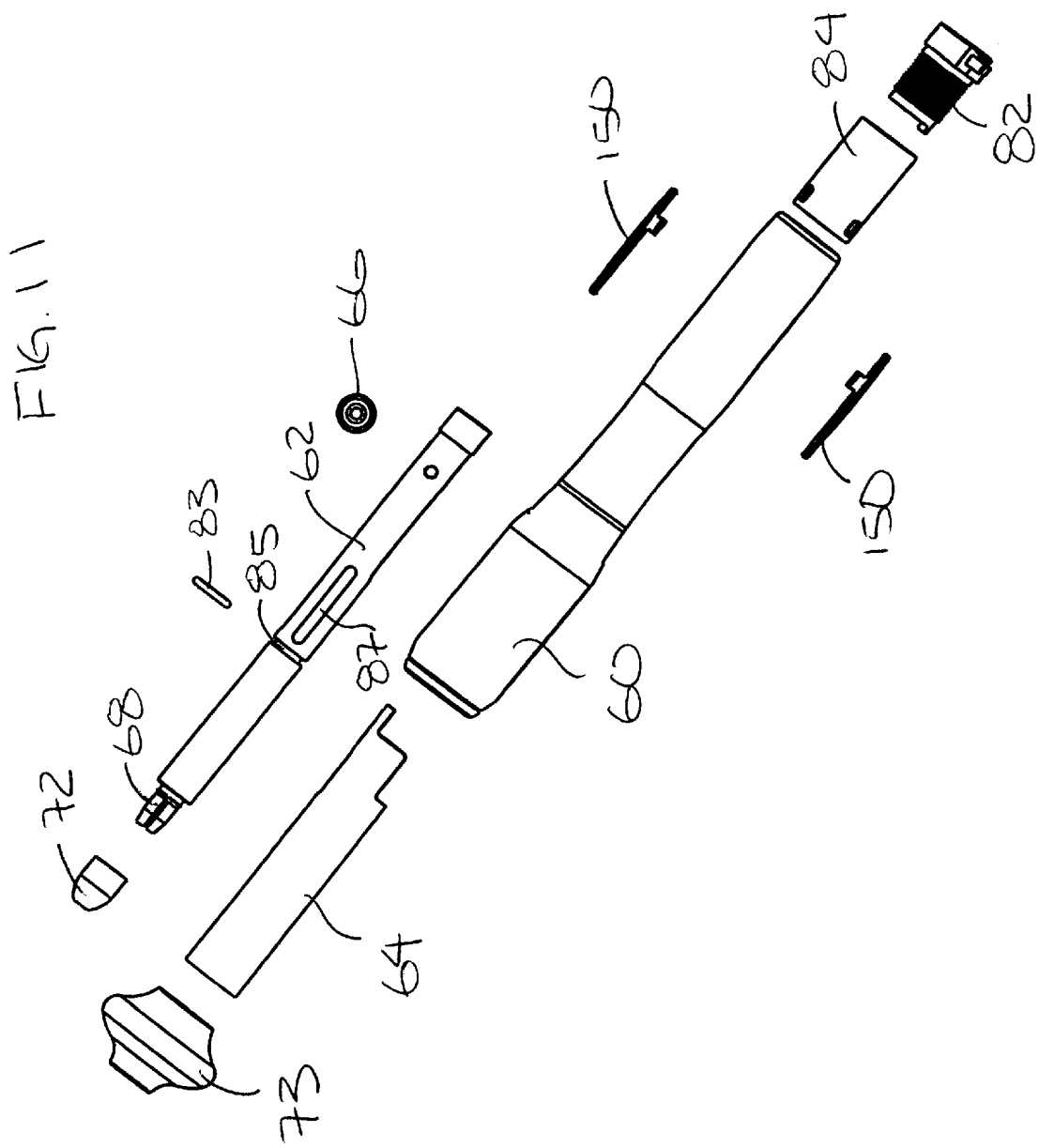

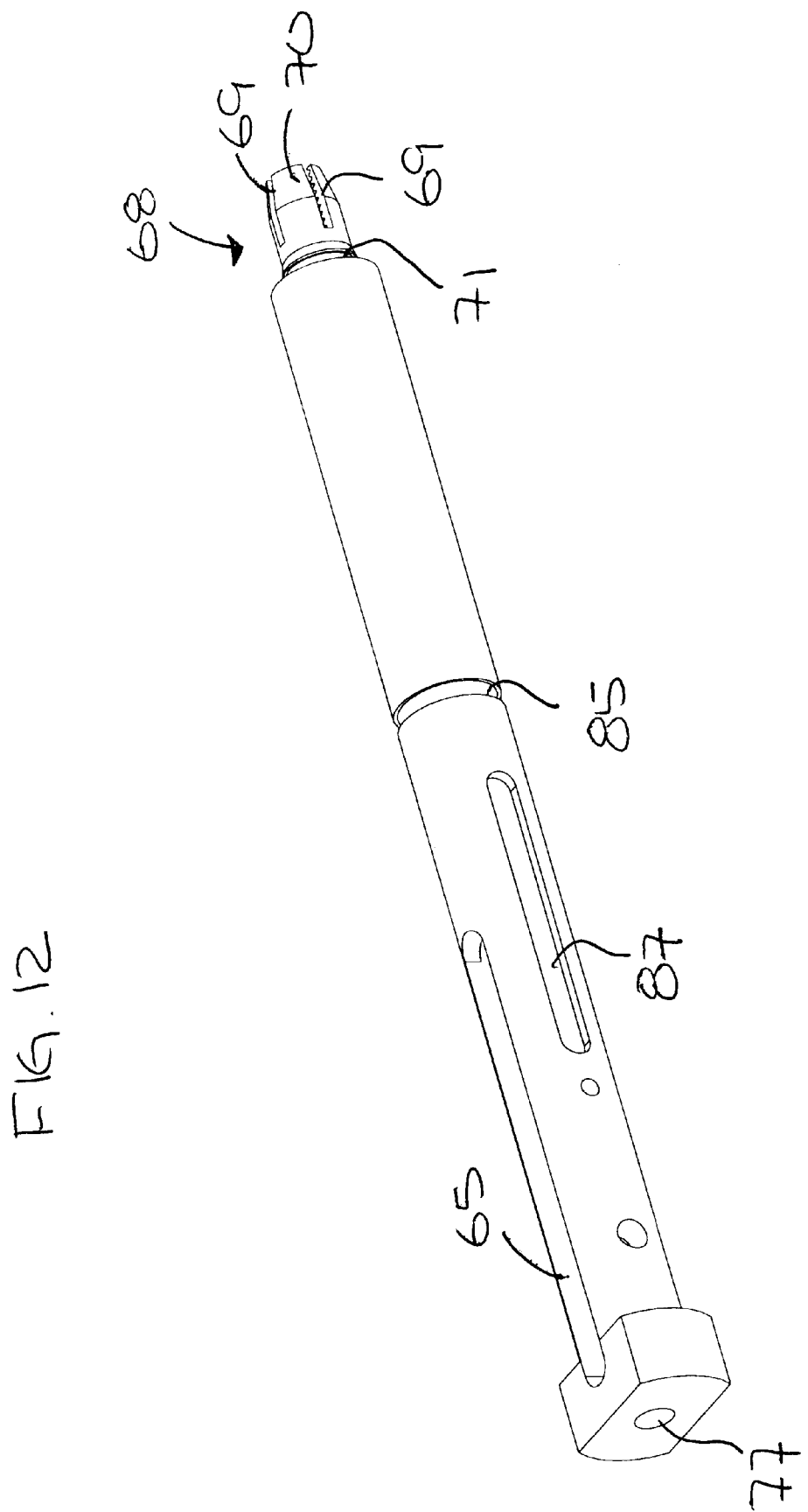

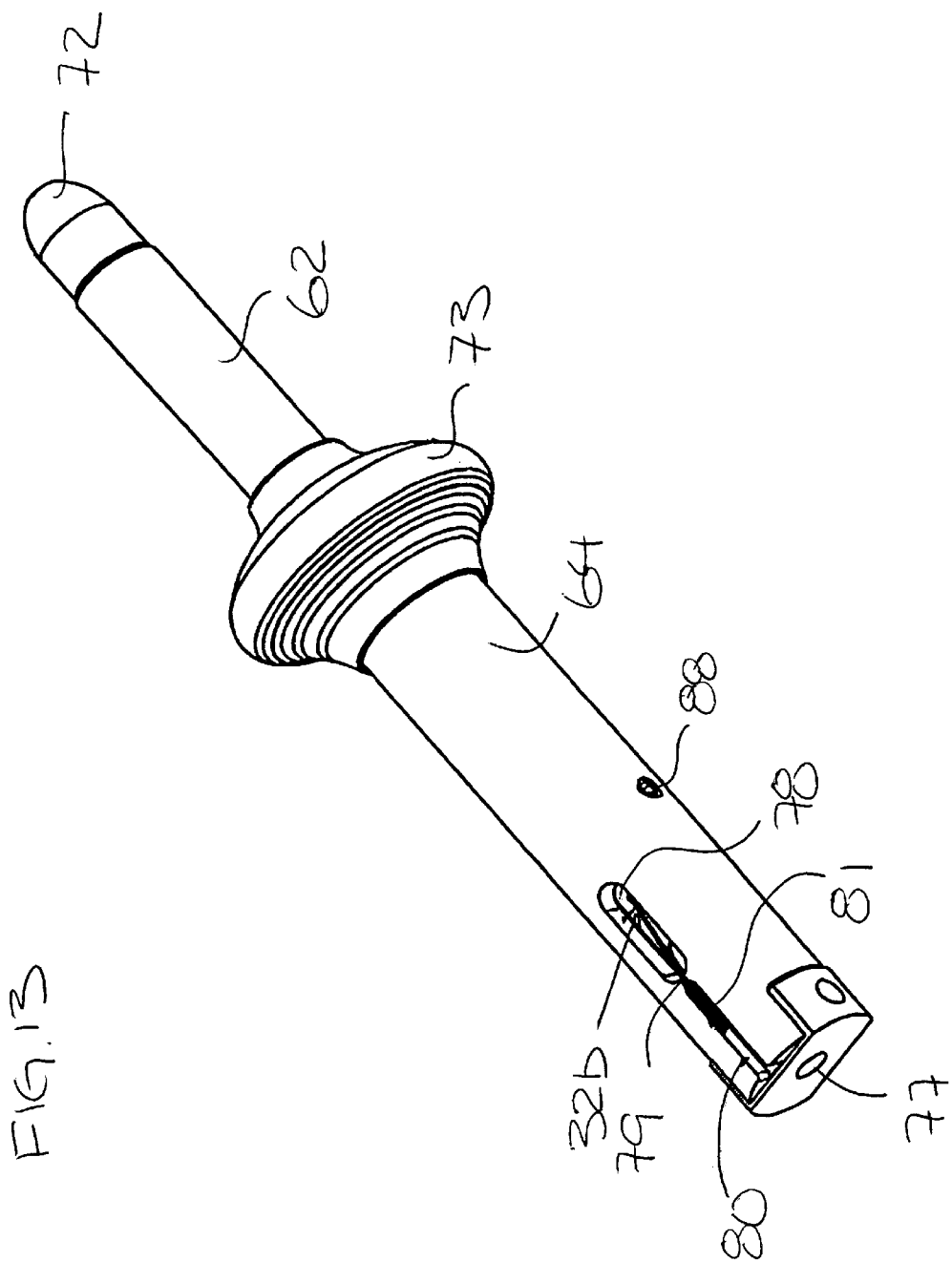

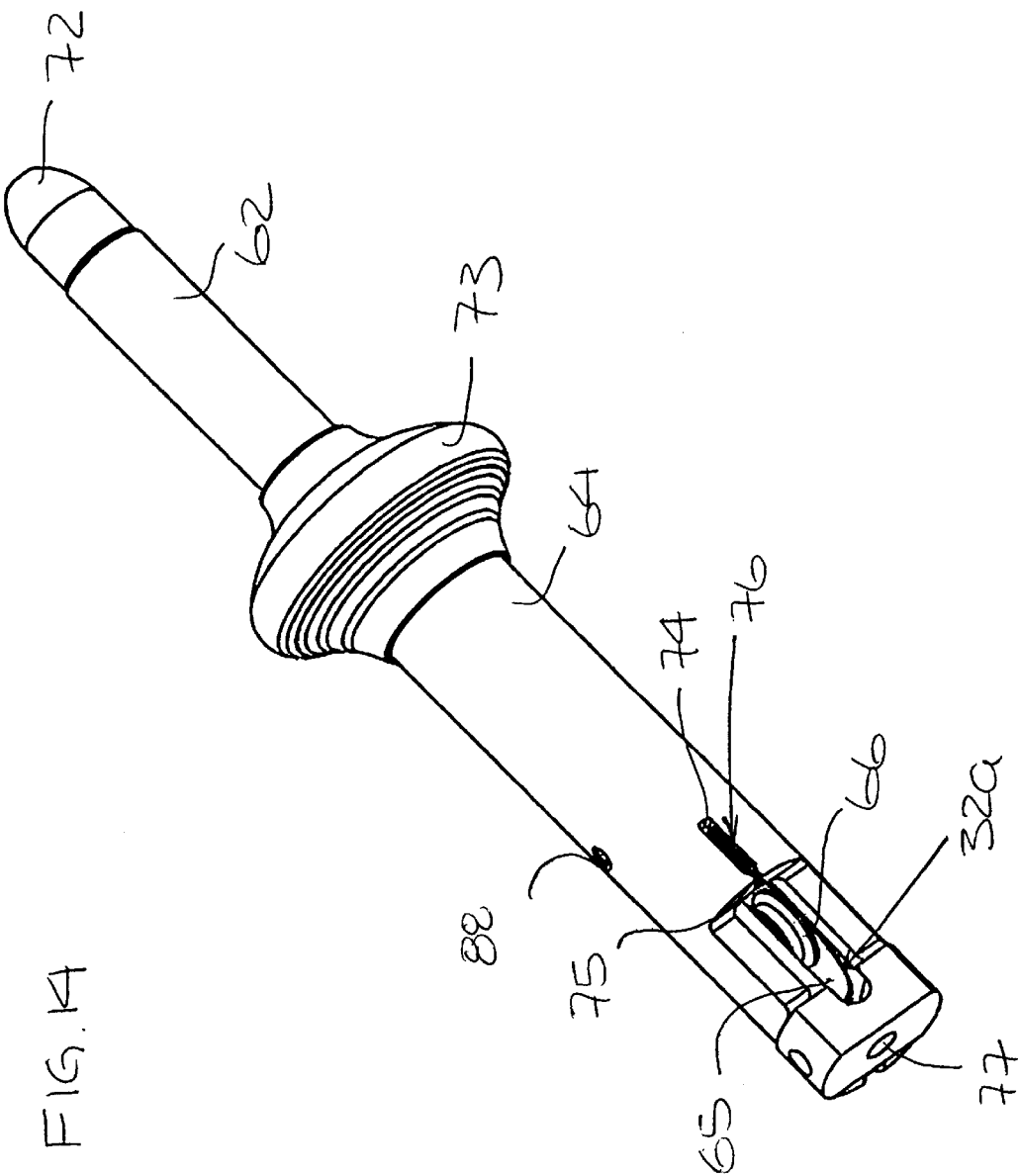

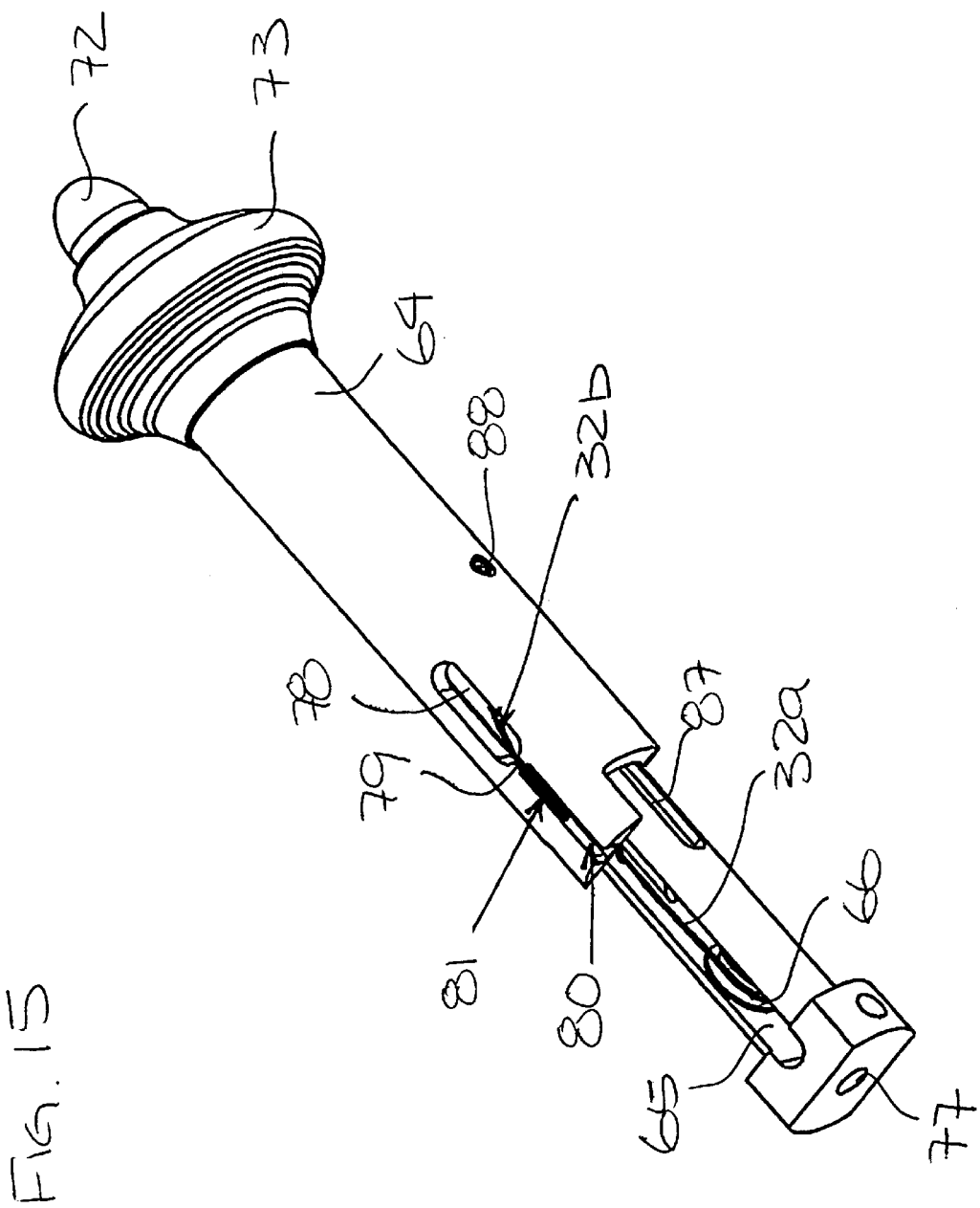

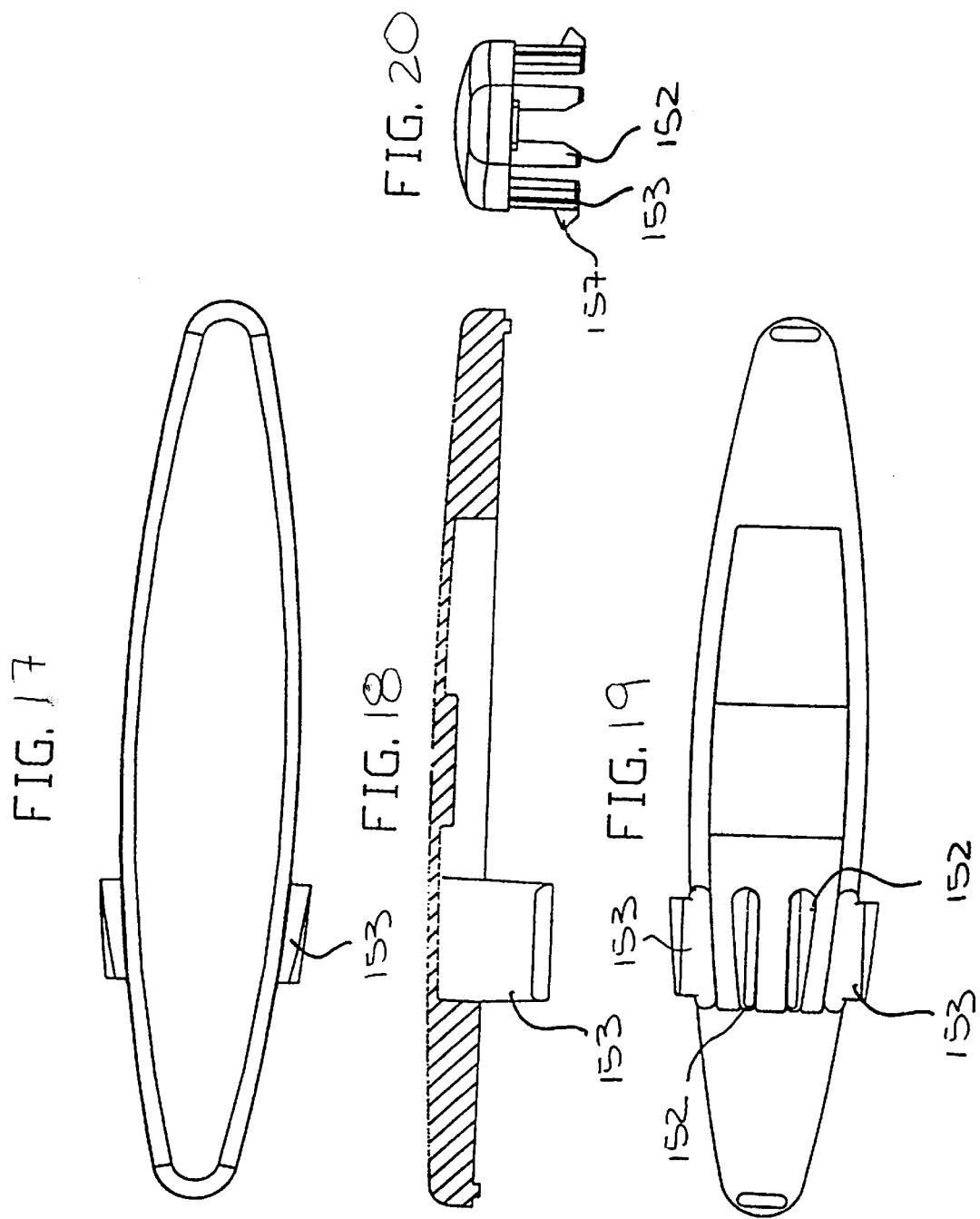

STEERABLE CATHETER WITH A CONTROL HANDLE HAVING A PULLEY MECHANISM

FIELD OF THE INVENTION

The present invention relates to an improved control handle for a bidirectional steerable catheter.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

The design described in RE 34,502 is generally limited to a catheter having a single puller wire. If a bidirectional catheter is desired, i.e., a catheter that can be deflected in more than one direction without rotating the catheter body, more than one puller wire becomes necessary. When two puller wires are used, however, it is undesirable for both wires to be moved simultaneously. The handle design disclosed in RE 34,502 is not suitable for a two puller wire system. Accordingly, a need exists for a control handle capable of independently moving each of two puller wires but preventing simultaneous movement of the puller wires.

SUMMARY OF THE INVENTION

The invention is directed to a steerable catheter having two puller wires and a control handle for manipulating the puller wires, and more preferably a bidirectional steerable catheter. In one embodiment, the catheter comprises an elongated, flexible tubular catheter body having proximal and distal ends and a lumen extending therethrough and a control handle at the proximal end of the catheter body. The control handle comprises a handle housing having a generally hollow interior and fixedly attached, either directly or indirectly to the catheter body; a piston slidably mounted in the handle housing and having proximal and distal ends; and a pulley fixedly attached, either directly or indirectly to the handle housing at a location proximal to the proximal end of the piston. A first puller wire is provided having a distal end fixedly attached in the distal end of the catheter body and a proximal end anchored to the piston. A second puller wire is provided having a distal end fixedly attached in the distal end of the catheter body. The second puller wire extends through the catheter body, into the handle, and around the pulley, and the proximal end of the second puller wire is anchored to the piston. By this design, simultaneous deflection of both puller wires can be avoided.

DESCRIPTION OF THE DRAWINGS

These and other features of the advantages of the present invention will be better understood by reference to the following detailed description when considered in conjunction with the accompanying drawings wherein:

FIG. 1 is a side view of an embodiment of the catheter of the invention.

FIG. 2 is a side cross-sectional view of the junction of the catheter body and tip section of an embodiment of a catheter according to the invention.

FIG. 3 is a transverse cross-sectional view of the catheter body shown in FIG. 2 taken along line 3—3.

FIG. 9 is a side cross-sectional view of a handle in accordance with the invention.

FIG. 10 is a side view of the handle of FIG. 9.

FIG. 11 is a side schematic view of the components of the handle of FIGS. 9 and 10 when the handle is not assembled.

FIG. 12 is a perspective view of the inner rod of the handle of FIGS. 9 to 11.

FIG. 13 is a perspective view of the piston and inner rod of the inventive handle positioned to place tension on the second puller wire.

FIG. 14 is a perspective view showing the opposite side of the piston and inner rod of FIG. 13.

FIG. 15 is a perspective view of the piston and inner rod of the inventive handle positioned to place tension on the first puller wire.

FIG. 17 is a top view of a fastener for use with the inventive handle.

FIG. 18 is a side view of a fastener for use with the inventive handle.

FIG. 19 is a bottom view of a fastener for use with the inventive handle.

FIG. 20 is an end view of a fastener for use with the inventive handle.

DETAILED DESCRIPTION

Figure 4:
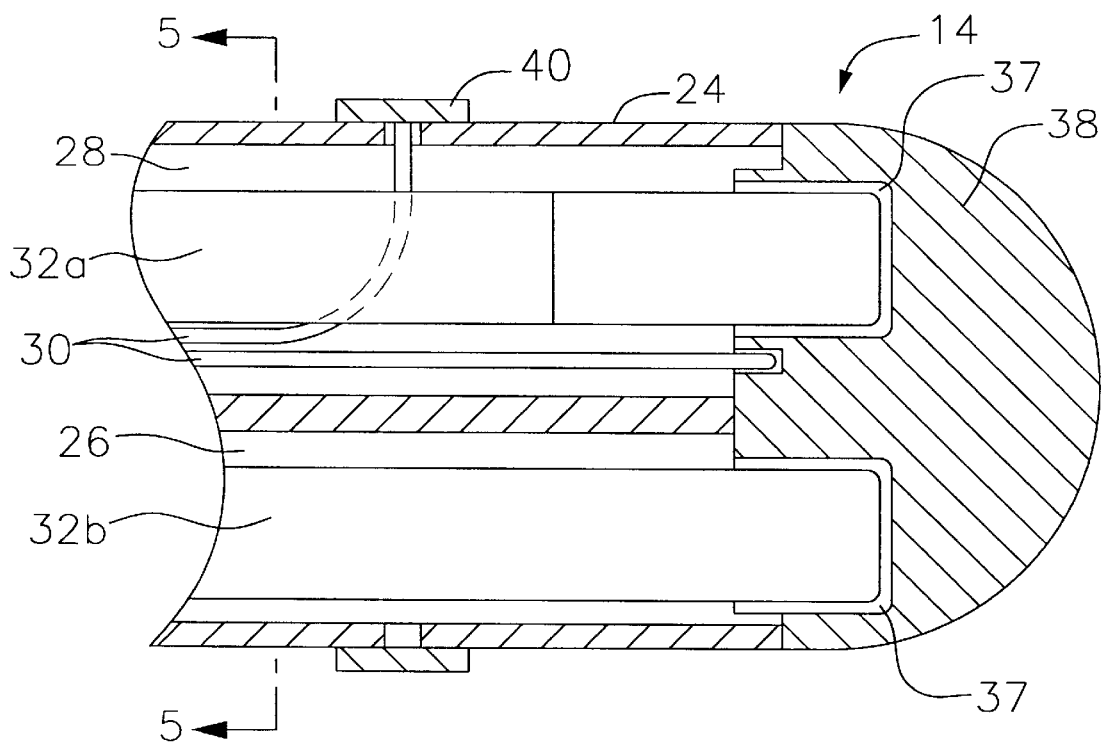
FIG. 4 is a side cross-sectional view of the distal end of the tip section shown in FIG. 2.

In a particularly preferred embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch. If desired, the stiffening tube can be omitted.

Figure 5:
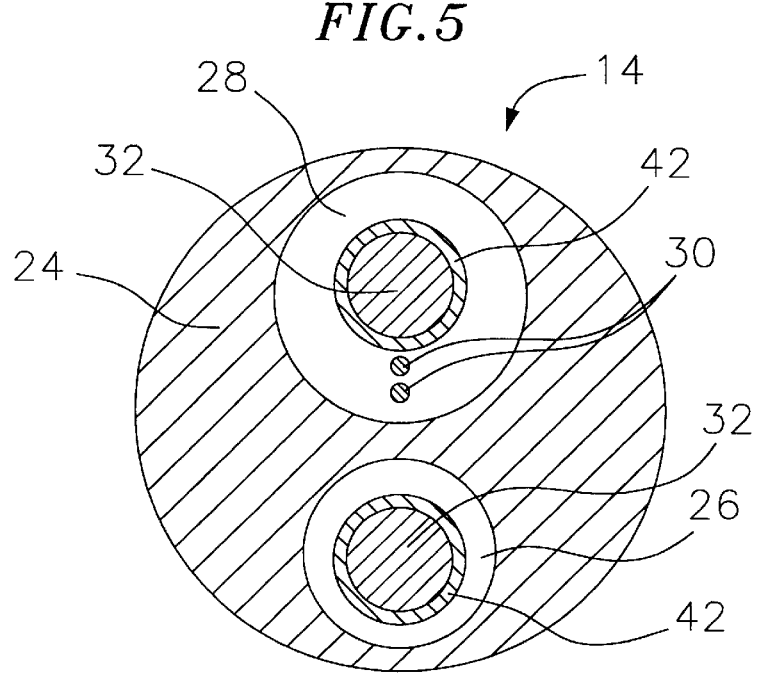
FIG. 5 is a transverse cross-sectional view of the tip section along line 5—5.

As shown in FIGS. 4 and 5, the tip section 14 comprises a short section of flexible tubing 24 having a first off-axis lumen 26 and a second off-axis lumen 28. The flexible tubing 24 is made of a suitable non-toxic material that is preferably more flexible than the catheter body 20. A presently preferred material for the tubing 24 is braided polyurethane, i.e., polyurethane with an embedded mesh of braided stainless steel or the like. The outer diameter of the tip section 14, like that of the catheter body 12, is preferably no greater than about 8 french, more preferably about 6½ french or less.

The off-axis lumens 26, 28 extend through diametrically opposed halves of the tip section 14. In the depicted embodiment, the off-axis lumens 26, 28 are asymmetrical and therefore non-interchangeable. The first off-axis lumen 26 is smaller than the second off-axis lumen 28. In an 8 French or 7 French diameter catheter, where the tip section is 6½ French, it is preferred that the first off-axis lumen 26 has a diameter ranging from about 0.018 inch to about 0.025 inch, more preferably from about 0.018 inch to about 0.022 inch. Preferably, the second off-axis lumen 28 has a diameter ranging from about 0.022 inch to about 0.030 inch, more preferably from about 0.026 inch to about 0.028 inch. By using two rather than three lumens along a single diameter, the present design retains the simplified construction of the unidirectional deflectable steerable catheter described in U.S. Pat. No. Re 34,502, which is incorporated herein by reference. However, the number and size of the lumens in the tip section is not critical to the present invention and can vary as desired.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast drying glue, e.g. Super Glue®. Thereafter a second glue joint is formed between the proximal ends of the stiffening tube 22 and outer wall 20 using a slower drying but stronger glue, e.g., polyurethane.

A spacer 36 lies within the catheter body 12 between the distal end of the stiffening tube 22 and the proximal end of the tip section 14. The spacer 36 is preferably made of a material that is stiffer than the material of the tip section 14, e.g., polyurethane, but not as stiff as the material of the stiffening tube 22, e.g. polyimide. A spacer made of Teflon® is presently preferred. A preferred spacer 36 has a length of from about 0.25 inch to about 0.75 inch, more preferably about 0.50 inch. Preferably the spacer 36 has an outer and inner diameter about the same as the outer and inner diameters of the stiffening tube 22. The spacer 36 provides a transition in flexibility at the junction of the catheter body 12 and the tip section 14 to bend smoothly without folding or kinking. If desired, the spacer 36 can be omitted.

As shown in FIG. 4, the distal end of the tip section 14 carries a tip electrode 38. Mounted along the length of the tip section 14 is a ring electrode 40. The length of the ring electrode 40 is not critical, but preferably ranges from about 1 mm to about 3 mm. Additional ring electrodes can be provided if desired. If multiple ring electrodes are used, they are spaced apart in any fashion as desired so long as their edges do not touch.

The tip electrode 38 and ring electrode 40 are each connected to a separate lead wire 30. Each lead wire 30 extends through the second off-axis lumen 28 in the tip section 14, through the central lumen 18 in the catheter body 12 and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like. Connection of a lead wire 30 to a ring electrode 40 is preferably accomplished by first making a small hole through the tubing 24. Such a hole can be created, for example, by inserting a needle through the tubing 24 and heating the needle sufficiently to form a permanent hole. A lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like.

Two puller wires 32 extend through the catheter 10. Each puller wire 32 extends from the control handle 16, through the central lumen 18 in the catheter body 12 and into one of the off-axis lumens 26 and 28 of the tip section 16. As described in more detail below, the proximal end of each puller wire 32 is anchored within the control handle 16 and the distal end of each puller wire 32 is anchored within the tip section 14.

Each puller wire 32 is made of any suitable metal, such as stainless steel or Nitinol. Preferably each puller wire 32 has a coating, such as a coating of Teflon® or the like. Each puller wire 32 has a diameter preferably ranging from about 0.006 inch to about 0.0010 inch. Preferably both of the puller wires 32 have the same diameter.

Each puller wire 32 is anchored near the distal end of the tip section 14. In the embodiment depicted in FIG. 4, the puller wires 32 are both anchored in blind holes 37 in the tip electrode 38 by a welding or the like.

Figure 6:
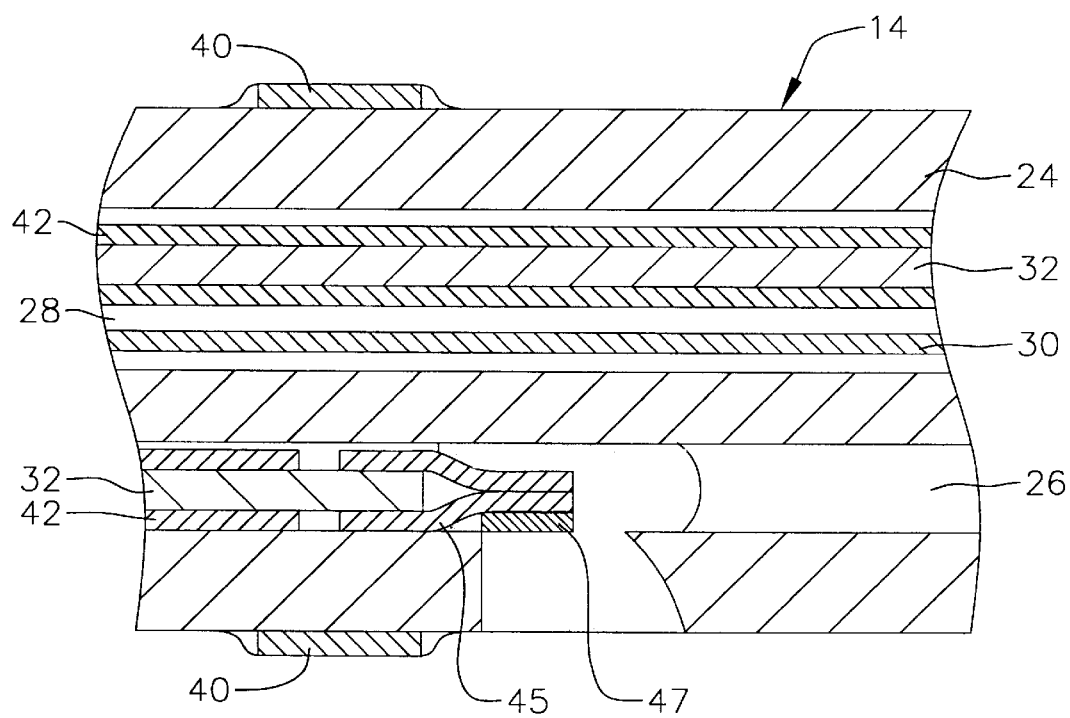
FIG. 6 is a transverse cross-sectional view of a catheter tip section according to the invention where the puller wires are anchored to the side walls of the tip section.
Figure 7:
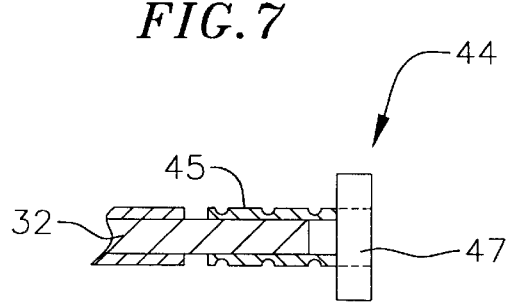
FIG. 7 is a longitudinal cross-sectional view of a preferred puller wire T-bar anchor.
Figure 8:
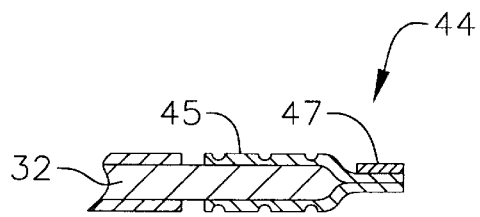
FIG. 8 is a longitudinal cross-sectional view of the puller wire T-bar anchor of FIG. 7 rotated 90° to show the cross-piece on end.

Alternatively, the puller wire 32 in the first off-axis lumen 26 can be anchored to the side wall of the tip section 14. As shown in FIGS. 6 to 8, the puller wire 32 is preferably attached by means of an anchor 44 fixedly attached to the distal end of the puller wire 32. The anchor 44 is formed by a metal tube 45, e.g., a short segment of hypodermic stock, that is fixedly attached, e.g. by crimping, to the distal end of the puller wire 32. The tube has a section that extends a short distance beyond the distal end of the puller wire 32. A cross-piece 47 made of a small section of stainless steel ribbon or the like is soldered or welded in a transverse arrangement to the distal end of the metal tube which is flattened during the operation. This creates a T-bar anchor 44. A notch is created in the side of the tip section 14 resulting in an opening in the off-axis lumen 26 carrying the puller wire 32. The cross piece 47 lies transversely within the notch. Because the length of the ribbon forming the cross-piece 47 is longer than the diameter of the opening into the off-axis lumen 26, the anchor 44 cannot be pulled completely into the off-axis lumen 26. The notch is then sealed with polyurethane glue or the like to give a smooth outer surface. The glue flows into the off-axis lumen 26 to fully secure the anchor. A tunnel (not shown), in the form of polyimide tubing or the like, can be provided to permit passage of the lead wire 30 through the glue so that this same puller wire anchor construction can be used in the second off-axis lumen 28. Other means for anchoring the puller wires 32 in the tip section 14 would be recognized by those skilled in the art and are included within the scope of the invention.

In the depicted embodiment, the distal ends of the puller wires 32 are attached to opposite sides of the tip section 14. This design permits deflection of the tip section 14 in opposing directions. Alternatively, the puller wires 32 could be attached at different locations about the circumference of the tip section 14 that are not opposing, permitting deflection in two different directions, although not opposing directions. In another embodiment, the puller wires 32 can be attached at different locations along the length of the tip section 14, i.e., with the distal end of one puller wire anchored proximal the distal end of the other puller wire. Such a design would permit deflection at different points along the length of the tip section. Any combination of these anchor positions can be provided in accordance with the invention.

The catheter 10 further comprises two compression coils 46, each in surrounding relation to a corresponding puller wire 32, as shown in FIGS. 2 and 3. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. A non-conductive sheath 48 made of thin-walled polyimide tubing is presently preferred.

At the distal end of the catheter body, the two compression coils 46 are positioned in diametric opposition within the stiffening tube 22 and spacer 36 so that they can be aligned with the two off-axis lumens 26,28 in the tip section 14. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

The distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 26,28 of the tip section 14 and are anchored at their distal ends to the proximal end of the tip section 14 by a glue joint. In the depicted embodiment, where the compression coils 46 are each surrounded by a sheath 48, care should be taken to insure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

Both glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 18 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care must be taken to insure that glue does not wick over the end of the coil so that the puller wire cannot slide within the coil.

Within the off-axis lumens 26, 28, each puller wire 32 is surrounded by a plastic sheath 42, preferably made of Teflon®. The plastic sheathes 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Longitudinal movement of a puller wire 32 relative to the catheter body 12, which results in deflection of the tip section 14, is accomplished by suitable manipulation of the control handle 16. A suitable bidirectional control handle for use in the present invention is illustrated in FIGS. 9 to 11. The control handle 16 comprises a generally-hollow, preferably generally-tubular, handle housing 60 having a longitudinal axis and proximal and distal ends, a generally tubular inner rod 62 extending within the housing along its longitudinal axis, and a generally tubular piston 64 also mounted in the handle housing in surrounding relation to the inner rod. The inner rod 62 is fixedly attached to the handle housing 60 with a set screw (not shown) and to the catheter body 12, as described in more detail below.

The piston 64 is mounted is slidable relation to the inner rod 62, and thus is moveable relative to the catheter body 12. As discussed in more detail below, the proximal ends of the puller wires 32 are attached to the piston 64 so that longitudinal movement of the piston relative to the inner rod 62 and catheter body 12 correspondingly moves the puller wires 32 relative to the catheter body. A circumferential groove 85 is provided near the midsection of the inner rod 62 in which an o-ring 83 is mounted to provide a tight fit between the inner rod and the piston 64. A thumb knob 73 is mounted in surrounding relation to the piston 64 to assist the user with longitudinal movement of the piston relative to the inner rod 62. Additionally, a rubber grip 86 is provided in surrounding relation to the handle housing 60 near the middle of the handle to provide comfort to the user.

The tubular inner rod 62, shown in more detail in FIG. 12, has a generally hollow interior at its distal end, forming a passage 63 through which the puller wires 32 extend. At its very distal end, the inner rod 62 has a grip mechanism 68 for attachment of the catheter body 12. The grip mechanism 68 is generally tubular with longitudinal slits 69 creating compressible sections 70 therebetween. Proximal to the compressible sections 70 are threads 71 for receiving an end cap 72. The end cap 72 has inner threads (not shown) to permit the end cap to screw onto the grip mechanism 68. The catheter body 12 fits through a longitudinal hole in the end cap 72 and a longitudinal hole in the grip mechanism 68 and is secured within the grip mechanism 68 by the compression of the compressible sections 70 when the end cap is threaded onto the grip mechanism.

Figure 16:
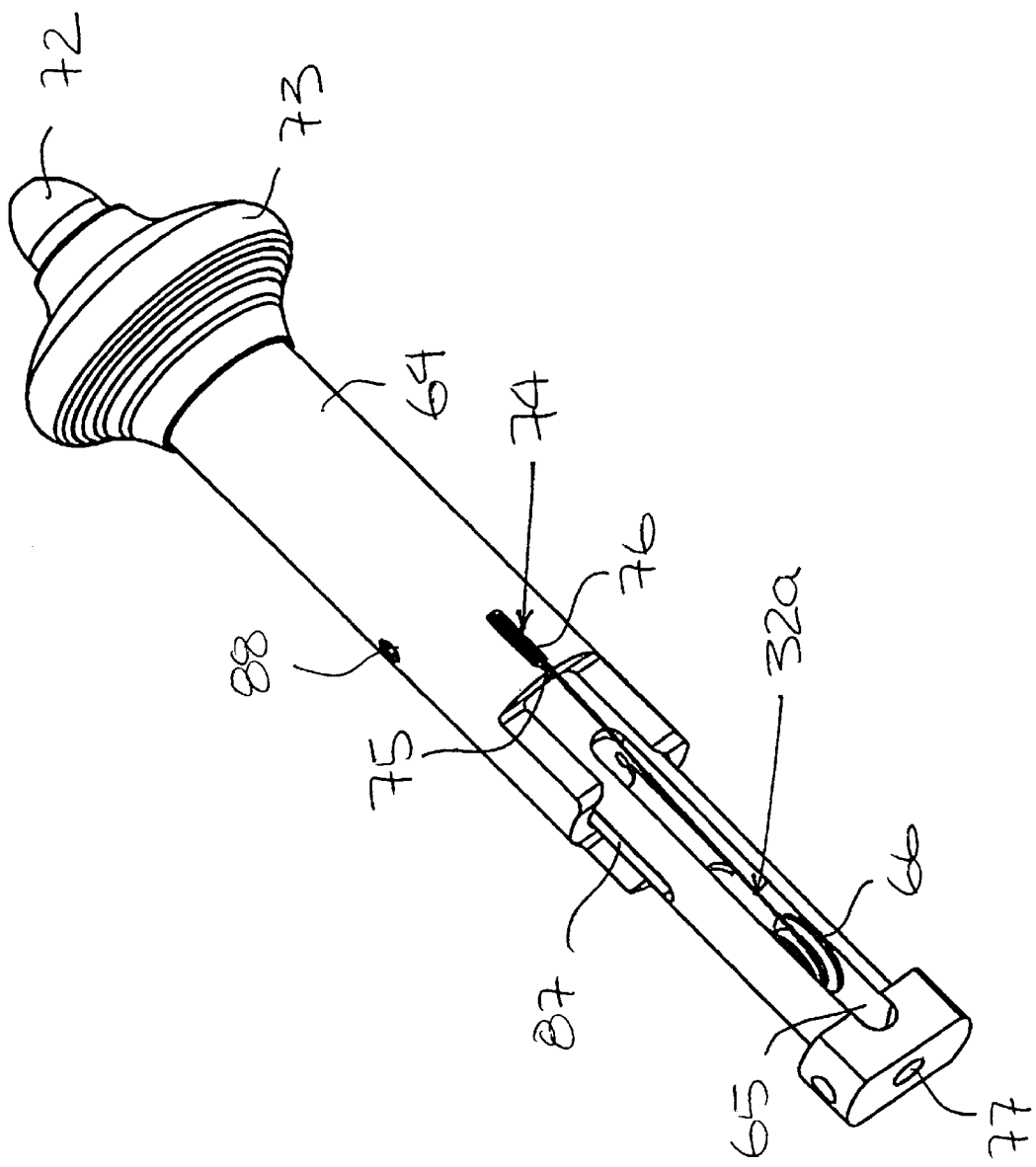
FIG. 16 is a perspective view showing the opposite side of the piston and inner rod of FIG. 15.

At its proximal end, the inner rod 62 has a longitudinal slot 65 extending through the diameter of the rod. A pulley 66 is mounted in the longitudinal slot 65 with a dowel pin 67. The first puller wire 32a extends through the passage 63 in the inner rod and around the pulley 66 and has its proximal end attached to the piston 64, as best shown in FIG. 16. Specifically, the piston 64 has a first slot 74 near its proximal end having a width greater than the width of the first puller wire 32a and a thinner groove 75 proximal the first slot. The first puller wire 32a extends through the thinner groove 75 and into the first slot 74. A first slug 76, e.g., a short piece of hypodermic stock, having a diameter greater than the diameter of the first puller wire 32a, is mounted on the proximal end of the first puller wire and snap-fit in the first slot 74. The slug 76 has a diameter greater than the width of the groove 75, thereby anchoring the first puller wire 74 to the piston 64. Distal movement of the piston 64 relative to the inner rod 62 pulls the first puller wire 32a, which extends around the pulley 66, proximally relative to the inner rod and catheter body 12, resulting in deflection of the tip section 14 in the direction of the side to which the distal end of the first puller wire is anchored.

The second puller wire 32b also extends through the passage 63 of the inner rod 62 and is attached directly to the piston 64, as shown in FIGS. 13 and 15. The second puller wire 32b extends through the passage 63 and longitudinal slot 65 of the inner rod and through an opening 78 in the sidewall of the piston 64. The opening 78 is on the side of the piston 64 opposite the first slot 74. A second slot 80 is provided on the outside of the piston 64 proximal to the opening 78 with a second thinner groove 79 provided therebetween. The second puller wire 32b extends out of the opening 78, through the second thinner groove 79, and into the second slot 80. A second slug 81 having a diameter greater than the diameter of the second puller wire 32b is mounted on the proximal end of the second puller wire and slidably positioned in the second slot 80. The second slug 81 has a diameter greater than the width of the second thinner groove 79, thereby anchoring the second puller wire to the piston 64. Proximal movement of the piston 64 relative to the inner rod 62 pulls the second puller wire 32b proximally relative to the inner rod and catheter body 12, resulting in deflection of the tip section 14 in the direction of the side to which the distal end of the second puller wire is anchored.

FIGS. 13 to 16 show the relationship of the inner rod 62, piston 64 and puller wires 32 in use. When the catheter is in the neutral position, i.e., when the tip section 14 is not deflected, the inner rod 62 and piston 64 are positioned such that tension is not placed on either puller wire 32. FIGS. 13 and 14 show the piston 64 positioned distally relative to its neutral position on the inner rod 62. As a result, the second puller wire 32b is pulled proximally relative to the catheter body 12, as shown in FIG. 13, and no tension is placed on the first puller wire 32a, as shown in FIG. 14. Accordingly, the tip section 14 is deflected in the direction of the side to which the distal end of the second puller wire 32b is anchored. In contrast, FIGS. 15 and 16 shows the piston 64 positioned proximally relative to its neutral position on the inner rod 62. As a result, the first puller wire 32a is pulled proximally relative to the catheter body 12, as shown in FIG. 16, and no tension is placed on the second puller wire 32b, as shown in FIG. 15. Accordingly, the tip section 14 is deflected in the direction of the side to which the distal end of the first puller wire 32a is anchored. As shown in FIG. 15, the second slot 80 is longer than the second slug 81 to provide for relaxation of the second puller wire 32b.

The electrode lead wires 30 extend through the passage 63 of the inner rod 62, through the longitudinal slot 65, out a hole 77 at the proximal end of the inner rod, and through the interior of the proximal end of the handle housing 60, and terminate at their proximal ends in a connector 82. The connector 82 is mounted to the handle housing 60 by means of a connector adapter 84 to which the connector is screwed.

Figure 21:
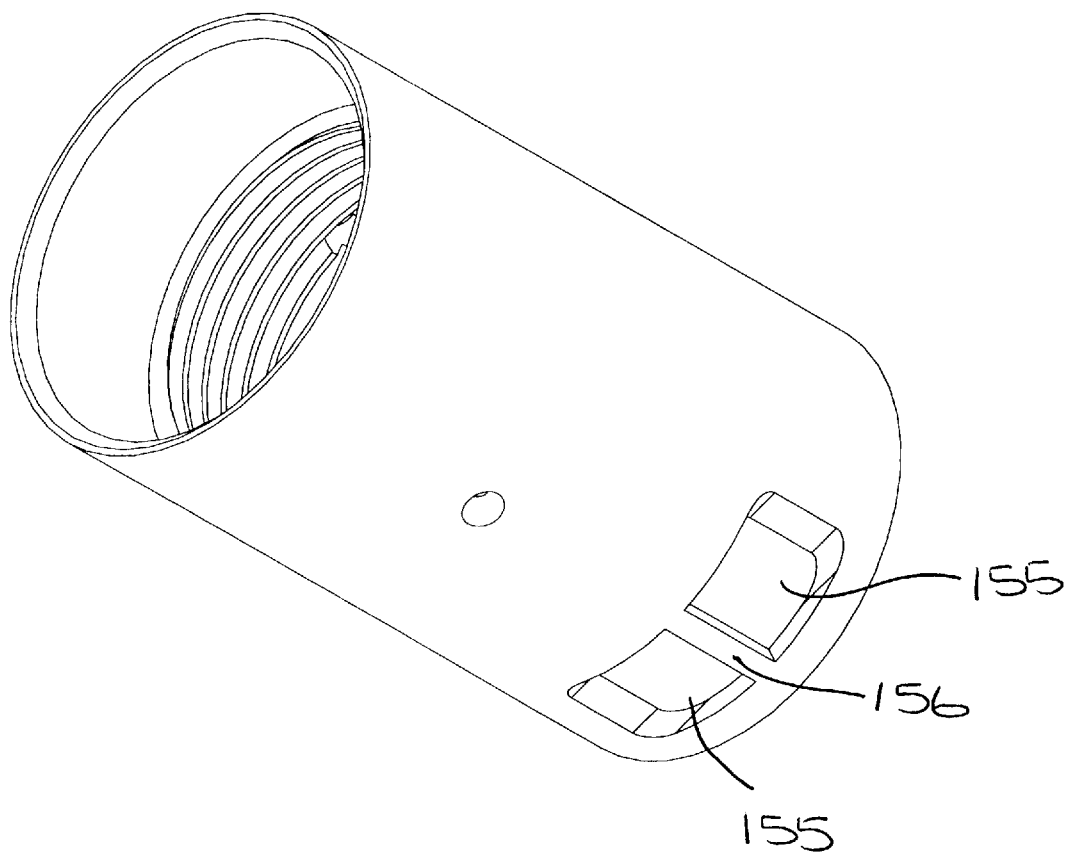
FIG. 21 is a perspective view of a connector adapter for use in connection with the handle of the invention.

Two fasteners 150 are provided to maintain the handle housing 60 in place over the connector adapter 84. FIGS. 17 to 20 show a preferred fastener 150 in accordance with the invention. The fastener 150 has a generally ovular (or jewel) shape. The top side, as shown in FIG. 17, is generally flat, but may be slightly curved to match the curved contour of the handle housing 60. The bottom side, as shown in FIGS. 18 to 20, comprises two inner prongs 152 and two outer prongs 153. The prongs 152 and 153 are received by the connector adapter, as shown in FIG. 9. Specifically, the adapter 84 comprises two pairs of recesses 155 separated by a tab 156, as shown in FIG. 21, with the pairs of recesses on opposite sides of the adapter. Each set of prongs 152 and 153 extends into corresponding recesses 155, and the inner prongs 152 fit tightly around the corresponding tab 156 to maintain the fastener 150 in place.

As shown in FIGS. 9 and 10, the handle housing 60 comprises two openings 154 on opposite sides of the housing, each opening corresponding in size and shape to the corresponding fastener 150. When the handle is assembled, the fastener 150 is snapped into place in the handle housing, with the prongs 152 and 153 being received by the adapter 84, keeping the handle housing in place over the adapter. The outer prongs 153 comprise outwardly extending ears 157. When a fastener is snapped into a corresponding opening 154 of the housing 60, the ears 157 extend under the opening to keep the fastener in place in the handle housing. The fastener also provides a means for engraving or labeling the handle. The fastener can be provided with a design, trademark, or other insignia relevant to the catheter, thus making it unnecessary to manufacture the handle housing with the insignia directly thereon.

A mechanism is provided for creating sufficient friction between the piston 64 and the inner rod 62. Specifically, a slot 87 is provided through the side wall of the inner rod 62. A nylon-tipped set screw (not shown) extends through a hole 88 in the outer wall of the piston 64 and into the slot 87 of the inner rod 62. As the piston 64 is moved laterally relative to the inner rod 62, the nylon-tipped set screw causes friction between the two components. When the tip section 14 is deflected, this friction holds the piston 64 in place relative to the inner rod 62 to maintain the deflection even if the user releases the handle.

Figure 22:
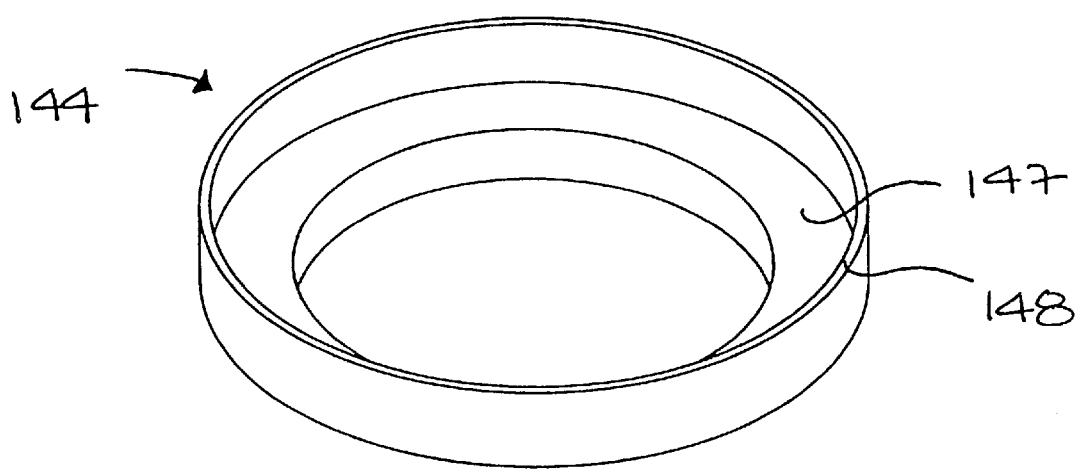
FIG. 22 is a perspective view of a washer according to the invention.
Figure 23:
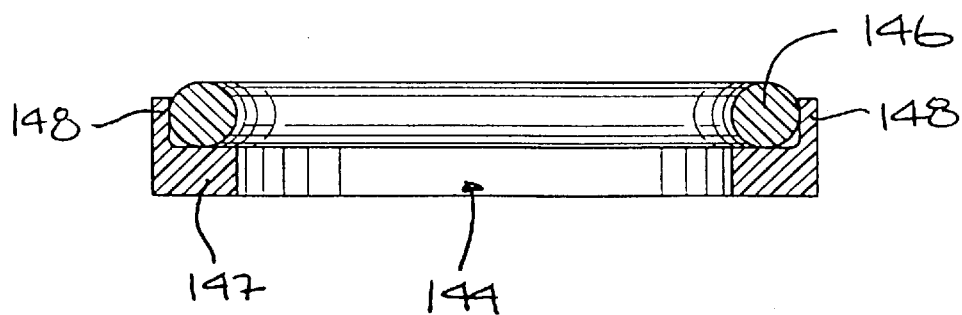
FIG. 23 is a cross-sectional view of an o-ring mounted in a washer according to the invention.

In an alternative embodiment, a mechanism for the user to adjust the tension of the thumb control 73 is provided. The mechanism includes a washer 144 mounted about the inner rod 62 at the distal end of the piston 64. As shown in FIGS. 22 and 23, the washer 144 comprises a flat, O-shaped proximal ring 147 with an outer edge and an inner edge. An outer wall 148 extends distally from the outer edge of the proximal ring 147. By this design, the proximal end of the washer 144 is closed, but the distal end is open. The washer is preferably made out of the same material as the handle housing.

A flexible o-ring 146, made of plastic, rubber or the like, is provided having an outer surface, an inner surface, a proximal surface and a distal surface. The o-ring 146 sits in the open distal end of the washer 144 so that its proximal surface is in contact with the distal surface of the proximal ring of the washer, its outer surface is in contact with the outer wall 148, and its inner surface is in contact with the inner rod 62.

With this design, when the thumb control 73 is screwed onto the piston 64, it compresses the o-ring 146 into the washer 144, forcing the inner surface of the o-ring against the inner rod 62. The user can adjust the tension on the thumb control 73 by screwing or unscrewing the thumb control, thus adjusting the pressure of the thumb control on the o-ring. Alternatively, the washer can be integral with the distal end of the piston 64. In other words, the distal end of the piston 64 can be designed to incorporate a region into which the o-ring can fit to perform the same function, e.g., having a proximal ring and an outer wall extending distally from the proximal ring.

The preceding description has been presented with reference to presently preferred embodiments of the invention. Workers skilled in the art and technology to which this invention pertains will appreciate that alterations and changes in the described structure may be practiced /9without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable catheter comprising:
   an elongated, flexible tubular catheter body having proximal and distal ends and a lumen extending therethrough;
   a control handle at the proximal end of the catheter body, the handle comprising:
      a handle housing having a generally hollow interior and fixedly attached to the catheter body;
      a piston slidably and coaxially mounted in the handle housing and having proximal and distal ends, an outer wall, and a passage therethrough; and
      a pulley fixedly attached to the handle housing at a location proximal to the proximal end of the piston;
   a first puller wire having a distal end fixedly attached in the distal end of the catheter body and a proximal end anchored to the piston; and
   a second puller wire having a distal end fixedly attached in the distal end of the catheter body and extending through the catheter body, into the handle, and around the pulley, wherein the proximal end of the second puller wire is anchored to the piston.

2. A catheter according to claim 1, wherein the distal end of the first puller wire is attached to one side of the distal end of the catheter body and the distal end of the second puller wire is attached to the opposite side of the distal end of the catheter body.

3. A catheter according to claim 1, wherein the distal end of one puller wire is attached to the distal end of the catheter body at a first position and the distal end of the other puller wire is attached to the distal end of the catheter body at a second position proximal to the first position.

4. A catheter according to claim 1, wherein the proximal end of the first puller wire is anchored to one side of the piston and the proximal end of the second puller wire is anchored to the opposite side of the piston.

5. A catheter according to claim 1, wherein the handle housing and piston are generally tubular.

6. A catheter according to claim 1, further comprising a tip section at the distal end of the catheter body, the tip section comprising a flexible tubing that is more flexible than the catheter body and at least first and second off-axis lumens extending therethrough, wherein the first puller wire extends through the first off-axis lumen and the second puller wire extends through the second off-axis lumen.

7. A catheter according to claim 1, wherein the control handle further comprises an inner rod having proximal and distal ends and fixedly attached to the handle housing, wherein the piston is slidably mounted around the inner rod, the pulley is fixedly mounted on the inner rod, and the catheter body is fixedly attached to the distal end of the inner rod.

8. A catheter according to claim 7, wherein the handle housing, inner rod and piston are generally tubular.

9. A catheter according to claim 7, wherein the inner rod is generally tubular and has a passage extending through its distal end and a longitudinal slot extending through its proximal end, wherein the pulley is mounted in the slot.

10. A catheter according to claim 9, further comprising an electrode mounted at or near the distal end of the catheter body and an electrode lead wire having a distal end electrically connected to the electrode, extending through the catheter body, through the passage of the inner rod, and through the handle housing, and having a proximal end electrically connected to a suitable connector that is attached to the handle housing.

11. A catheter according to claim 1, wherein the first puller wire extends through the passage of the piston and out through an opening in the outer wall of the piston, whereby the proximal end of the first puller wire is anchored on the outside of the outer wall of the piston.

12. A catheter according to claim 11, wherein the piston includes a slot on the outer wall proximal the opening in the outer wall and a groove between the slot and the opening, wherein the groove has a width less than the width of the slot, and further wherein a slug having a width greater than the width of the slot is fixedly attached to the proximal end of the first puller wire and positioned within the groove, thereby anchoring the first puller wire to the piston.

13. A steerable catheter comprising:
an elongated, flexible tubular catheter body having proximal and distal ends and a lumen extending therethrough;
a control handle at the proximal end of the catheter body, the handle comprising:
a handle housing having a generally hollow interior and fixedly attached to the catheter body;
a piston slidably mounted in the handle housing and having proximal and distal ends, an outer wall, and a passage therethrough;
a pulley fixedly attached to the handle housing at a location proximal to the proximal end of the piston; and
an inner rod having proximal and distal ends and fixedly attached to the handle housing, wherein the piston is slidably mounted around the inner rod, the pulley is fixedly mounted on the inner rod, and the catheter body is fixedly attached to the distal end of the inner rod;
a first puller wire having a distal end fixedly attached in the distal end of the catheter body and a proximal end anchored to the piston; and
a second puller wire having a distal end fixedly attached in the distal end of the catheter body and extending through the catheter body, into the handle, and around the pulley, wherein the proximal end of the second puller wire is anchored to the piston.

14. A catheter according to claim 13, wherein the distal end of the first puller wire is attached to one side of the distal end of the catheter body and the distal end of the second puller wire is attached to the opposite side of the distal end of the catheter body.

15. A catheter according to claim 13, wherein the distal end of one puller wire is attached to the distal end of the catheter body at a first position and the distal end of the other puller wire is attached to the distal end of the catheter body at a second position proximal to the first position.

16. A catheter according to claim 13, wherein the proximal end of the first puller wire is anchored to one side of the piston and the proximal end of the second puller wire is anchored to the opposite side of the piston.

17. A catheter according to claim 13, wherein the handle housing and piston are generally tubular.

18. A catheter according to claim 13, further comprising a tip section at the distal end of the catheter body, the tip section comprising a flexible tubing that is more flexible than the catheter body and at least first and second off-axis lumens extending therethrough, wherein the first puller wire extends through the first off-axis lumen and the second puller wire extends through the second off-axis lumen.

19. A catheter according to claim 13, wherein the handle housing, inner rod and piston are generally tubular.

20. A catheter according to claim 13, wherein the inner rod is generally tubular and has a passage extending through its distal end and a longitudinal slot extending through its proximal end, wherein the pulley is mounted in the slot.

21. A catheter according to claim 20, further comprising an electrode mounted at or near the distal end of the catheter body and an electrode lead wire having a distal end electrically connected to the electrode, extending through the catheter body, through the passage of the inner rod, and through the handle housing, and having a proximal end electrically connected to a suitable connector that is attached to the handle housing.

22. A catheter according to claim 13, wherein the first puller wire extends through the passage of the piston and out through an opening in the outer wall of the piston, whereby the proximal end of the first puller wire is anchored on the outside of the outer wall of the piston.

23. A catheter according to claim 22, wherein the piston includes a slot on the outer wall proximal the opening in the outer wall and a groove between the slot and the opening, wherein the groove has a width less than the width of the slot, and further wherein a slug having a width greater than the width of the slot is fixedly attached to the proximal end of the first puller wire and positioned within the groove, thereby anchoring the first puller wire to the piston.

24. A steerable catheter comprising:
an elongated, flexible tubular catheter body having proximal and distal ends and a lumen extending therethrough;
a control handle at the proximal end of the catheter body, the handle comprising:
a handle housing having a generally hollow interior and fixedly attached to the catheter body;
a piston slidably attached to the handle housing and having proximal and distal ends, an outer wall, and a passage therethrough, wherein a distal portion of the piston extends outside the handle housing;
a thumb control fixedly attached around an entire perimeter of the distal portion of the piston; and
a pulley fixedly attached to the handle housing at a location proximal to the proximal end of the piston;
a first puller wire having a distal end fixedly attached in the distal end of the catheter body and a proximal end anchored to the piston; and
a second puller wire having a distal end fixedly attached in the distal end of the catheter body and extending through the catheter body, into the handle, and around the pulley, wherein the proximal end of the second puller wire is anchored to the piston.

25. A catheter according to claim 24, wherein the distal end of the first puller wire is attached to one side of the distal end of the catheter body and the distal end of the second puller wire is attached to the opposite side of the distal end of the catheter body.

26. A catheter according to claim 24, wherein the distal end of one puller wire is attached to the distal end of the catheter body at a first position and the distal end of the other puller wire is attached to the distal end of the catheter body at a second position proximal to the first position.

27. A catheter according to claim 24, wherein the proximal end of the first puller wire is anchored to one side of the piston and the proximal end of the second puller wire is anchored to the opposite side of the piston.

28. A catheter according to claim 24, wherein the handle housing and piston are generally tubular.

29. A catheter according to claim 24, further comprising a tip section at the distal end of the catheter body, the tip section comprising a flexible tubing that is more flexible than the catheter body and at least first and second off-axis lumens extending therethrough, wherein the first puller wire extends through the first off-axis lumen and the second puller wire extends through the second off-axis lumen.

30. A catheter according to claim 24, wherein the control handle further comprises an inner rod having proximal and distal ends and fixedly attached to the handle housing, wherein the piston is slidably mounted around the inner rod, the pulley is fixedly mounted on the inner rod, and the catheter body is fixedly attached to the distal end of the inner rod.

31. A catheter according to claim 30, wherein the handle housing, inner rod and piston are generally tubular.

32. A catheter according to claim 30, wherein the inner rod is generally tubular and has a passage extending through its distal end and a longitudinal slot extending through its proximal end, wherein the pulley is mounted in the slot.

33. A catheter according to claim 32, further comprising an electrode mounted at or near the distal end of the catheter body and an electrode lead wire having a distal end electrically connected to the electrode, extending through the catheter body, through the passage of the inner rod, and through the handle housing, and having a proximal end electrically connected to a suitable connector that is attached to the handle housing.

34. A catheter according to claim 24, wherein the first puller wire extends through the passage of the piston and out through an opening in the outer wall of the piston, whereby the proximal end of the first puller wire is anchored on the outside of the outer wall of the piston.

35. A catheter according to claim 34, wherein the piston includes a slot on the outer wall proximal the opening in the outer wall and a groove between the slot and the opening, wherein the groove has a width less than the width of the slot, and further wherein a slug having a width greater than the width of the slot is fixedly attached to the proximal end of the first puller wire and positioned within the groove, thereby anchoring the first puller wire to the piston.

* * * * *